(12) United States Patent
Witt et al.

(10) Patent No.: US 9,823,226 B2
(45) Date of Patent: Nov. 21, 2017

(54) HPLC SAMPLE INTRODUCTION WITH COUPLING SAMPLE RESERVOIRS IN PARALLEL BETWEEN MOBILE PHASE DRIVE AND SEPARATION UNIT

(71) Applicant: Agilent Technologies, Inc., Santa Clara, CA (US)

(72) Inventors: Klaus Witt, Keltern (DE); Konstantin Shoykhet, Karlsruhe (DE); Manfred Berndt, Karlsruhe (DE)

(73) Assignee: Agilent Technologies, Inc., Santa Clara, CA (US)

( * ) Notice: Subject to any disclaimer, the term of this patent is extended or adjusted under 35 U.S.C. 154(b) by 61 days.

(21) Appl. No.: 14/898,392

(22) PCT Filed: Jun. 14, 2013

(86) PCT No.: PCT/IB2013/054885
§ 371 (c)(1),
(2) Date: Dec. 14, 2015

(87) PCT Pub. No.: WO2014/199201
PCT Pub. Date: Dec. 18, 2014

(65) Prior Publication Data
US 2016/0139093 A1 May 19, 2016

(51) Int. Cl.
*G01N 1/00* (2006.01)
*G01N 30/00* (2006.01)
(Continued)

(52) U.S. Cl.
CPC ............ *G01N 30/20* (2013.01); *G01N 30/465* (2013.01); *G01N 2030/027* (2013.01); *G01N 2030/202* (2013.01); *G01N 2030/208* (2013.01)

(58) Field of Classification Search
USPC ........................................................ 73/61.56
See application file for complete search history.

(56) References Cited

U.S. PATENT DOCUMENTS 3,373,872 A * 3/1968 Hrdina .................. G01N 30/24
  210/198.2
4,625,569 A   12/1986 Toei et al.
(Continued)

FOREIGN PATENT DOCUMENTS

CN      201348625      11/2009
CN      102221584 A    10/2011
(Continued)

OTHER PUBLICATIONS

Notification of Transmittal of the International Search Report and the Written Opinion of the International Searching Authority for International Application No. PCT/IB2013/054885, dated Feb. 17, 2014.
(Continued)

*Primary Examiner* — Clayton E Laballe
*Assistant Examiner* — Warren K Fenwick

(57) ABSTRACT

Disclosed is a sample dispatcher configured for individually introducing a plurality of portions of one or more sample fluids into a flow of a mobile phase of a separation system configured for separating compounds of the sample fluids. The separation system comprises a mobile phase drive configured for driving the mobile phase through a separation unit configured for separating compounds of the sample fluids in the mobile phase. The sample dispatcher comprises a plurality of sample reservoirs, each configured for receiving and temporarily storing a respective sample fluid portion or at least a part thereof. The sample dispatcher is configured for selectively coupling one of the plurality of sample reservoirs between the mobile phase drive and the separation (Continued)

unit, and further for coupling at least two of the plurality of sample reservoirs in parallel between the mobile phase drive and the separation unit.

17 Claims, 8 Drawing Sheets

(51) Int. Cl.
  *G01N 30/20* (2006.01)
  *G01N 30/46* (2006.01)
  *G01N 30/02* (2006.01)

(56) References Cited

U.S. PATENT DOCUMENTS

| | | | | |
|---|---|---|---|---|
| 9,335,309 | B2* | 5/2016 | Witt | G01N 30/20 |
| 2009/0050212 | A1* | 2/2009 | Dourdeville | G01N 30/20 |
| | | | | 137/14 |
| 2012/0103074 | A1* | 5/2012 | Likuski | G01N 35/1097 |
| | | | | 73/61.55 |
| 2012/0285558 | A1* | 11/2012 | Witt | F04B 13/00 |
| | | | | 137/544 |
| 2013/0134095 | A1* | 5/2013 | Anderer | B01D 15/1878 |
| | | | | 210/656 |
| 2013/0276520 | A1* | 10/2013 | Moeller | F16K 11/0743 |
| | | | | 73/61.56 |
| 2014/0007660 | A1* | 1/2014 | Moeller | G01N 30/20 |
| | | | | 73/61.56 |
| 2014/0318224 | A1* | 10/2014 | Onoda | F04B 23/06 |
| | | | | 73/61.56 |
| 2014/0366739 | A1* | 12/2014 | Witt | B01D 15/14 |
| | | | | 96/182 |

FOREIGN PATENT DOCUMENTS

| | | |
|---|---|---|
| CN | 102792082 A | 11/2012 |
| CN | 102971567 A | 3/2013 |
| EP | 1536228 A1 | 6/2005 |
| WO | 2006083776 A2 | 8/2006 |
| WO | 2008150763 A1 | 12/2008 |
| WO | 2012175111 A1 | 7/2012 |

OTHER PUBLICATIONS

Chinese Office action dated Oct. 10, 2016 from related Chinese Patent Application No. 201380077405.9.

* cited by examiner

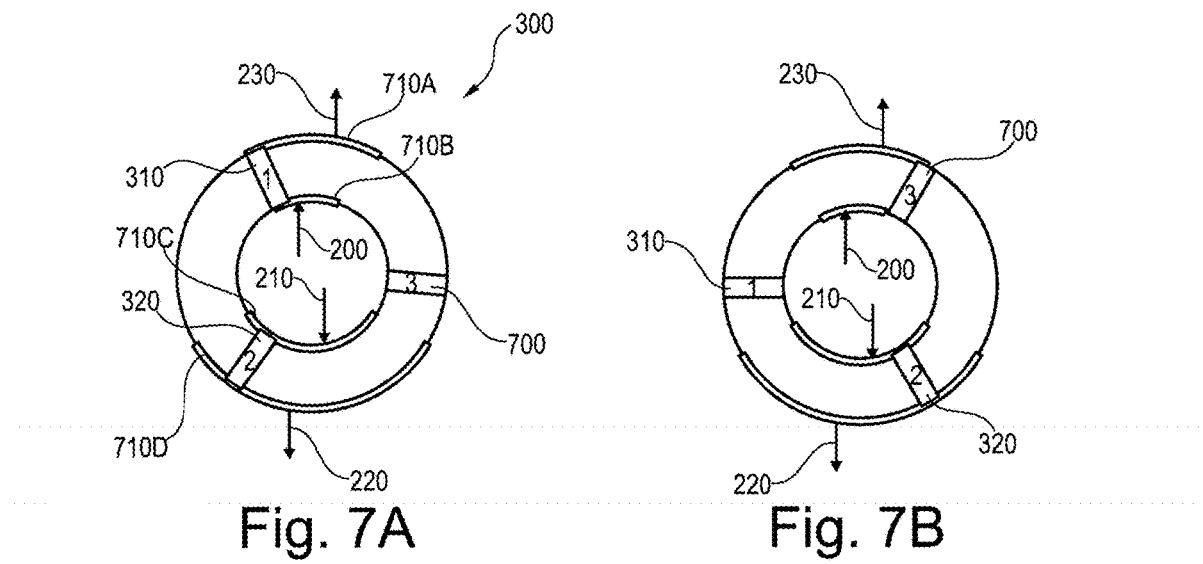
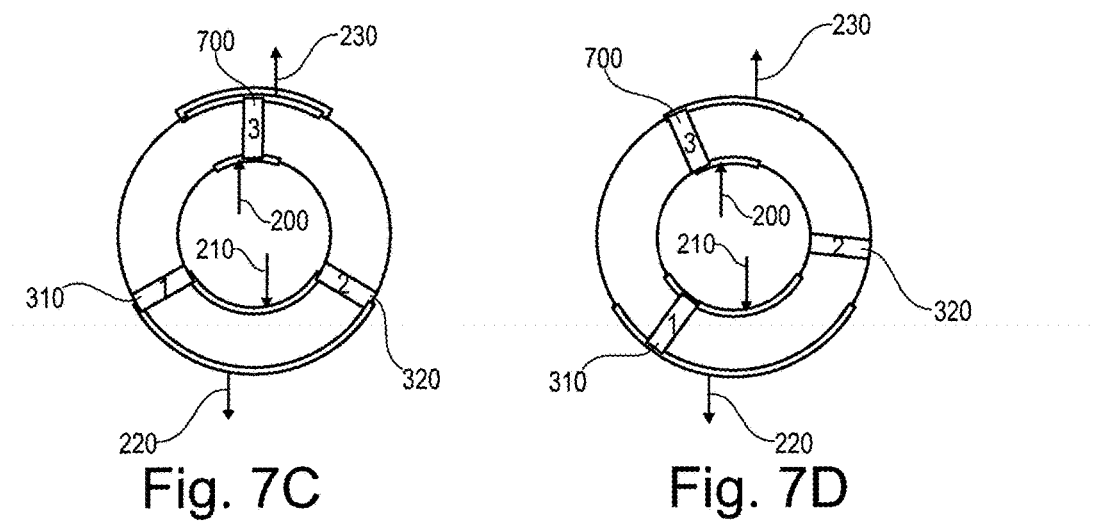

HPLC SAMPLE INTRODUCTION WITH COUPLING SAMPLE RESERVOIRS IN PARALLEL BETWEEN MOBILE PHASE DRIVE AND SEPARATION UNIT

RELATED APPLICATIONS

This application is the national stage of International Application No. PCT/IB2013/054885, filed Jun. 14, 2013, titled "HPLC SAMPLE INTRODUCTION WITH COUPLING SAMPLE RESERVOIRS IN PARALLEL BETWEEN MOBILE PHASE DRIVE AND SEPARATION UNIT," the content of which is incorporated herein by reference in its entirety.

BACKGROUND ART

The present invention relates to sample introduction and management, in particular in a high performance liquid chromatography application such as one-dimensional or two-dimensional HPLC.

In high performance liquid chromatography (HPLC), a liquid has to be provided usually at a very controlled flow rate (e. g. in the range of microliters to milliliters per minute) and at high pressure (typically 20-100 MPa, 200-1000 bar, and beyond up to currently 200 MPa, 2000 bar) at which compressibility of the liquid becomes noticeable. For liquid separation in an HPLC system, a mobile phase comprising a sample fluid (e.g. a chemical or biological mixture) with compounds to be separated is driven through a stationary phase (such as a chromatographic column packing), thus separating different compounds of the sample fluid which may then be identified. The term compound, as used herein, shall cover compounds which might comprise one or more different components.

The mobile phase, for example a solvent, is pumped under high pressure typically through a chromatographic column containing packing medium (also referred to as packing material or stationary phase). As the sample is carried through the column by the liquid flow, the different compounds, each one having a different affinity to the packing medium, move through the column at different speeds. Those compounds having greater affinity for the stationary phase move more slowly through the column than those having less affinity, and this speed differential results in the compounds being separated from one another as they pass through the column. The stationary phase is subject to a mechanical force generated in particular by a hydraulic pump that pumps the mobile phase usually from an upstream connection of the column to a downstream connection of the column. As a result of flow, depending on the physical properties of the stationary phase and the mobile phase, a relatively high pressure drop is generated across the column.

The mobile phase with the separated compounds exits the column and passes through a detector, which registers and/or identifies the molecules, for example by spectrophotometric absorbance measurements. A two-dimensional plot of the detector measurements against elution time or volume, known as a chromatogram, may be made, and from the chromatogram the compounds may be identified. For each compound, the chromatogram displays a separate curve feature also designated as a "peak". Efficient separation of the compounds by the column is advantageous because it provides for measurements yielding well defined peaks having sharp maxima inflection points and narrow base widths, allowing excellent resolution and reliable identification and quantitation of the mixture constituents. Broad peaks, caused by poor column performance, so called "Internal Band Broadening" or poor system performance, so called "External Band Broadening" are undesirable as they may allow minor components of the mixture to be masked by major components and go unidentified.

Two-dimensional separation of a fluidic sample denotes a separation technique in which a first separation procedure in a first separation unit is performed to separate a fluidic sample into a plurality of fractions, and in which a subsequent second separation procedure in a second separation unit is performed to further separate the plurality of fractions into sub-fractions. Two-dimensional liquid chromatography (2D LC) may combine two liquid chromatography separation techniques. When performing a 2D LC measurement, operation of two pumps needs to be coordinated in itself and with the action of further system components managing the sample and fraction transport, for instance with correspondingly switching fluidic valves. The sample and fraction pathway switching may result in pressure ripples or dips acting on separation units and other components of the fluid separation system, thereby deteriorating the chromatographic performance, reliability of the system and longevity of its components.

In so-called Comprehensive 2D LC, all eluate coming from the first dimension (e.g. the entire solvent flow containing the sample components past separation in the first chromatographic column) is coupled into the second dimension and further separated there. This significantly increases the requirements for processing speed in the second dimension. Typically, the solvent flow (containing the sample components) is fed into the second dimension in portions (also referred to as "sniplets"). Cycle times for processing of a single sniplet can be as fast as 15 seconds or lower. In such case with 4 cycles per minute, 24 hours of continued work means 5760 modulations or sample injections, which may come close to the lifetime of a column under usual operation conditions. In a number of arrangements the first dimension, or generally a sniplet source, provides sample contained in a solvent which may be too strong for the downstream dimension (e.g. for the second dimension). This can occur, e.g., when using HILIC in first dimension and RP (reversed phase) chromatography in second dimension, so it may be of advantage to dilute the sample plug (sniplet) coming from the collection loop before it hits the column.

Columns can be sensitive to flow disruptions and e.g. to reconnections with sample loops which hold lower pressure than the column itself (flow reversal due to backwards de-compression of the column content). Also the column may be sensitive to abrupt (re)connection to high pressure sources, resulting in pressure shocks on the column and packing material deterioration. These can be substantial factors of column aging, wear and deterioration.

Sample introduction in HPLC systems is disclosed e.g. in U.S. Pat. No. 3,916,692A, WO2006083776A2, U.S. Pat. No. 8,047,060B2.

WO2012175111A1, by the same applicant, discloses a two-dimensional HPLC system.

DISCLOSURE

It is an object of the invention to provide an improved sample introduction, in particular for one- and two-dimensional HPLC applications.

According to an embodiment of the present invention, a sample dispatcher is configured for individually introducing a plurality of portions of one or more sample fluids into a flow path and thus into a flow of a mobile phase of a separation system. The separation system is configured for separating compounds of the sample fluid(s) and comprises a mobile phase drive configured for driving the mobile phase through a separation unit, whereby the separation unit is configured for separating compounds contained in the sample fluid(s) as those are driven through the separation unit by the mobile phase. The sample dispatcher comprises a plurality of sample reservoirs, each configured for individually receiving and temporarily storing a respective portion of sample fluid or a part (or components) thereof. Such sample reservoir may be any kind of volume allowing to receive and temporarily store the respective sample fluid portion, such as a container, sample loop, capillary tube, injection needle, microfluidic device, planar fluidic device, cartridge, packed cartridge, trap column, etc. The sample dispatcher is configured for selectively coupling one of the plurality of sample reservoirs between the mobile phase drive and the separation unit.

The sample dispatcher may also work as and/or be referred to as a flow dispatching apparatus or a sample introduction apparatus.

The sample dispatcher is further configured for coupling at least two of the plurality of sample reservoirs in parallel between the mobile phase drive and the separation unit. Embodiments of the present invention thus allow dilution of the respective sample fluid portion with the mobile phase and may also allow reducing or even avoiding pressure variations occurring at the separation unit (in particular when switching between the plurality of sample reservoirs to be coupled between the mobile phase drive and the separation unit).

In one embodiment, the sample dispatcher is configured for coupling at least two of the plurality of sample reservoirs in parallel between the mobile phase drive and the separation unit during a dilution state of changing from having one of the plurality of sample reservoirs being coupled between the mobile phase drive and the separation unit to further having another one of the plurality of sample reservoirs being coupled between the mobile phase drive and the separation unit. In other words, the dilution state comprises changing from having one of the sample reservoirs being coupled between the mobile phase drive and the separation unit to having at least one further sample reservoir being coupled (in parallel to the already coupled sample reservoir) between the mobile phase drive and the separation unit, whereas one of the sample reservoirs coupled in parallel contains sample at least for a part of the time interval of the said parallel coupling. This may allow at least one of:

Diluting the respective sample fluid portion with the mobile phase during the dilution state;

Maintaining the dilution state at least for a time interval sufficient for displacement of at least a part of the content of the plurality of sample reservoirs (which are currently coupled between the mobile phase drive and the separation unit) simultaneously into a common fluid conduit;

Changing composition of a respective sample fluid portion having temporarily been stored in one of the plurality of sample reservoirs by mixing with the content displaced out of at least another one of the plurality of sample reservoirs when displaced into a common conduit;

Pressure relief (also referred to as decompressing) of a respective sample reservoir after having been coupled between and subsequently decoupled from the mobile phase drive and the separation unit and before being coupled for receiving and temporarily storing a respective sample fluid portion or at least a part thereof;

Precompressing a respective sample reservoir before being coupled between the mobile phase drive and the separation unit and after being coupled for receiving and temporarily storing a respective sample fluid. Coupling a first and a second terminal of a sample-containing sample reservoir to the mobile phase drive and to the separation unit respectively may be arranged in a defined order/sequence (in time). This can unify the direction of shifting of the sample zone within the sample-containing sample reservoir e.g. caused by the elasticity of the sample reservoir and compressibility of its content as the sample reservoir is connected to high pressure lines.

Dilution may be achieved during the dilution state when at least one of the sample reservoirs (coupled in parallel between the mobile phase drive and the separation unit) contains sample fluid (and a respective content of the sample fluid portion is being transferred into the common fluid conduit) while at least one of the sample reservoirs (coupled in parallel between the mobile phase drive and the separation unit) preferably does not contain sample fluid. At least the downstream part of the preferably non-sample-containing sample reservoir should preferably contain an essentially sample-free mobile phase at that moment or period in time, when the downstream part of the sample-containing sample reservoir contains the sample fluid. The volume of the mobile phase which flows out of the preferably non-sample-containing reservoir dilutes the sample fluid portion as the latter flows out of the sample-containing sample reservoir and is joined with the mobile phase flow at the downstream joining point of said parallel connection. It is clear that the degree (or ratio) of dilution can be controlled e.g. by the flow ratio through the sample reservoirs, and by the length of the time period of the dilution state, however, of course only as long as sample fluid is still at least partially contained in the respective sample reservoir(s) during the dilution state.

Dilution can be in particular of advantage e.g. in case the respective sample fluid portion to be separated contains a solvent which may influence the separation in the separation unit. This may be the case e.g. in a 2D LC application, where the mobile phase of the first dimension may influence or deteriorate the separation in the second dimension if the dimensions are not sufficiently orthogonal, e.g. in case the first dimension is HILIC or normal phase and the second dimension is reversed phase (in which case the eluate of the first dimension is a strong or eluotropic solvent for the second dimension). The same can be valid in case of RP-chromatography in both dimensions. In particular in case the first dimension is operated in a gradient mode (wherein the ratio between at least two different solvents is varied over the time), such interference might vary during the course of the gradient mode, e.g. when going from non-organic to organic solvents, or vice versa.

It is clear that in case the dilution state is passed sufficiently fast, the effect of dilution might be low or even absent, which might be even applied on purpose e.g. as an intermediate state and/or for reduction for pressure pulsations.

In one embodiment the sample dispatcher is configured so that—essentially at any point in the time during operation—at least one of the plurality of sample reservoirs, either alone or in a parallel combination, is coupled between the mobile phase drive and the separation unit. This allows to maintain essentially continuous pressure and flow supply from the mobile phase drive to the separation unit, and thus to reduce or even avoid pressure variations (occurring at the separation unit). The respective sample reservoir/s allow/s maintaining the pressure and flow applied by the mobile phase drive to the separation unit, and may help avoiding that the separation unit is temporarily disconnected from the mobile phase drive(e.g. when switching between the sample reservoirs). This may allow reducing or even avoiding pressure variations (e.g. pressure drops or ripples) occurring at an inlet end of the separation unit. This can be of advantage because such pressure variations, especially abrupt pressure variations, may not only adversely affect separation as well as measurement accuracy and precision, but may even damage such separation unit (in particular in case a chromatographic column is applied therein).

The term "essentially continuous" or "essentially at any point in the time" as used here shall mean that the pressure and flow supply is not interrupted for longer than a given time interval, preferably not longer than 80 milliseconds, more preferably not longer than 20 milliseconds, and further preferably is not interrupted at all during operation.

Embodiments of the invention allow providing an improved sample introduction, in particular for one- and two-dimensional HPLC applications and other hyphenated technique application with high pressure separation technology in the downstream dimension such as, e.g., SPE-LC, continuous process control LC.

In one embodiment of the present invention, both suppression of pressure pulse(s) and dilution are provided by the sample dispatcher, which renders such embodiment in particular useful for 2D LC applications, in particular in comprehensive mode when all or substantially all eluate coming from the first dimension is coupled into the second dimension and further separated there.

In one embodiment, the sample reservoirs are configured each to be exchangeable or adjustable in its flow restrictivity, so that a flow ratio between a flow through the respective sample reservoirs (and thus a dilution ratio in such parallel connection) can be adjusted. The ratio of the flow restrictivity of the sample reservoirs determines the resulting flow ratio in parallel connection.

In one embodiment, the sample dispatcher receives the plurality of portions of one or more sample fluids and is configured for filling or loading a respective sample fluid portion into at least one of the sample reservoirs. The sample dispatcher may be operated to alternatingly load the sample reservoirs, so that at least one of the sample reservoirs can be loaded while the content of at least another one may be being transferred into the flow of the mobile phase.

Embodiments applied in a 2D LC application may allow substantially continuously processing (in the second dimension) of the eluate received from the first dimension by (substantially continuously) switching between loading one sample reservoir and introducing the content of another sample reservoir into the flow of the mobile phase of the second dimension.

In one embodiment, the sample dispatcher comprises a switching valve having a plurality of ports and a plurality of flow couplers. Each port is configured for coupling a fluid flow path to the switching valve, and each flow coupler is configured for fluidically coupling between at least two of the ports. The switching valve can be selectively operated between a plurality of different states, wherein in each different state at least one of the flow couplers is fluidically coupling a different port.

The mobile phase drive is coupled to a first port of the plurality of ports, the separation unit is coupled to a second port of the plurality of ports, a flow path for receiving the plurality of portions of the one or more sample fluids is coupled to a third port of the plurality of ports, the first sample reservoir is coupled to a forth and to a fifth port of the plurality of ports, and the second sample reservoir is coupled to a sixth and to a seventh port of the plurality of ports. An eighth port of the plurality of ports may be coupled to "waste", e.g. an output which is not used for further processing but simply represents waste.

A first one of the flow couplers is configured for coupling between the second, fifth and the sixth ports, and a second one of the flow couplers is configured for coupling between the first, fourth and seventh ports, so that at least two of the plurality of sample reservoirs are coupled in parallel between the mobile phase drive and the separation unit.

At least one of the flow couplers is preferably configured to couple the eighth port (coupled to waste) to a respective one of the sample reservoirs before the other end of this sample reservoir is coupled to the third port (provided for receiving the sample fluid). This may allow for pressure relief of this respective sample reservoir after having been coupled between and subsequently decoupled from the mobile phase drive and the separation unit and before being coupled for receiving and temporarily storing a respective sample fluid portion or at least a part thereof.

The sample dispatcher of the preceding embodiment may preferably be provided so that a first subset of the plurality of ports is arranged along an inner circle, a second subset of the plurality of ports is arranged along an outer circle having larger diameter than the inner circle, a first subset of the plurality of flow couplers is configured to couple between ports of the first subset of the plurality of ports, and a second subset of the plurality of flow couplers is configured to couple between ports of the second subset of the plurality of ports.

Preferably, the first subset of the plurality of ports has four ports, the second subset of the plurality of ports has four ports, the first subset of the plurality of flow couplers has two flow couplers, and the second subset of the plurality of flow couplers has two flow couplers.

More preferably, the ports are arranged symmetrically, and one of the flow couplers in each of the first and second subsets of the plurality of flow couplers is longer than the other in the same subset.

According to another aspect of the present invention, a separation system is provided for separating sample fluid compounds. The separation system comprises a first mobile phase drive, a sample providing apparatus, a first separation unit, and a sample dispatcher in accordance with any one of the aforementioned embodiments. The first mobile phase drive (which may be a pump or pumping system) is adapted to drive a first mobile phase through the separation system. The sample providing apparatus is configured to provide a plurality of portions of one or more sample fluids. The first separation unit, which may be a chromatographic column, is adapted for separating compounds of the sample fluid in the first mobile phase as those are passed through the first separation unit.

The sample dispatcher is coupled to the first mobile phase drive and to the sample providing apparatus and is configured to introduce the provided sample fluid portions into a flow of the mobile phase. The sample dispatcher is further configured to load a respective sample fluid portion into at least one of the one or more sample reservoirs (and preferably serially and alternatingly into different ones of the sample reservoirs). In such separation system, the sample dispatcher receives the sample fluid from the sample providing apparatus, and may alternatingly fill at least one sample reservoir while the content of the other sample reservoir(s) is being transferred into the flow of the first mobile phase (which may then be separated by the first separation unit).

In one embodiment, the sample providing apparatus of the separation system comprises a second mobile phase drive, which may also be a pump or pumping system and embodied in accordance with the first mobile phase drive, adapted to drive a second mobile phase through a second separation system. A second separation unit, which may also be a chromatographic column in accordance with the first separation unit, is provided adapted for separating compounds of the sample fluid in the second mobile phase. At least a portion of the compounds past separation are provided as the plurality of portions of one or more sample fluids. Such embodiment may be in particular useful in 2D LC applications, so that the sample providing apparatus may represent an embodiment of the first dimension of a 2D-LC system.

One embodiment according to the present invention is related to a method of individually introducing a plurality of portions of one or more sample fluids into a flow of a mobile phase of a separation system. The separation system is configured for separating compounds of the sample fluids and comprises a mobile phase drive and a sample dispatcher. The mobile phase drive is configured for driving the mobile phase through a separation unit for separating compounds of the sample fluids in the mobile phase. The sample dispatcher comprises a plurality of sample reservoirs, each configured for receiving and temporarily storing a respective sample fluid portion or at least a part thereof. The method comprises a step of selectively coupling one of the plurality of sample reservoirs between the mobile phase drive and the separation unit, and a further step of coupling at least two of the plurality of sample reservoirs in parallel between the mobile phase drive and the separation unit.

In one embodiment, the method further comprises coupling at least two of the plurality of sample reservoirs in parallel between the mobile phase drive and the separation unit during a dilution state. The dilution state comprises changing from having one more sample-containing sample reservoirs being coupled between the mobile phase drive and the separation unit to having at least one further sample reservoir being coupled (in parallel to the sample-containing sample reservoirs) between the mobile phase drive and the separation unit.

During the dilution state of the sample dispatcher, the respective sample fluid portion can be diluted with the mobile phase provided from the respective other sample reservoir(s).

The dilution state may be maintained at least for a time interval sufficient for displacement of at least a part of the content of the plurality of sample reservoirs (which are currently coupled between the mobile phase drive and the separation unit) simultaneously into a common fluid conduit.

Changing composition of a respective sample fluid portion temporarily contained in one of the plurality of sample reservoirs may be provided by mixing with the content displaced out of at least another one of the plurality of sample reservoirs.

A respective sample reservoir may be decompressed, i.e. the pressure within such sample reservoir is reduced (preferably to about ambient pressure), after having been coupled between the mobile phase drive and the separation unit with having subsequently been decoupled from both, and before being coupled for receiving and temporarily storing a respective sample fluid portion or at least a part thereof.

A respective sample reservoir may be precompressed, i.e. the pressure within such sample reservoir is increased (preferably to about a pressure provided by mobile phase drive or a pressure currently occurring at the separation unit), before being coupled between the mobile phase drive and the separation unit and after being coupled for receiving and temporarily storing a respective sample fluid. Coupling a first and a second terminal of a sample-containing sample reservoir to the mobile phase drive and to the separation unit respectively may be arranged in a defined order/sequence (in time). This can unify the direction of shifting of the sample zone within the sample-containing sample reservoir e.g. caused by the entrance of some additional amount of compressed fluid due to the elasticity of the sample reservoir and compressibility of its content as the sample reservoir is connected to fluid lines under pressure provided by mobile phase drive.

In one embodiment, the method further comprises coupling—essentially at any point in the time—at least one of the plurality of sample reservoirs, either alone or in a parallel combination, between the mobile phase drive and the separation unit, preferably in order to reduce variations in pressure occurring at the separation unit when changing between the plurality of sample reservoirs being coupled between the mobile phase drive and the separation unit.

The embodiments of the present invention are preferably applied in Two-Dimensional Liquid Chromatography, more preferably in Comprehensive 2D LC, wherein substantially all eluate coming from the first dimension (e.g. the entire solvent flow containing the sample components past separation in the first chromatographic column) is coupled into the second dimension and further separated there, preferably at run-time or in other words in on-line mode.

In embodiments, the sample dispatcher is configured to allow cycle times for processing of a single portion of sample fluid (also referred to as sniplet) in less than one minute, and preferably in 15 seconds or lower. Correspondingly, the sample dispatcher is configured to allow a frequency of sample portion introduction of more than one per minute (i.e. more than 16 mHz), and preferably one per 15 seconds (i.e. more than 60 mHz) and higher.

Embodiments of the present invention might be embodied based on most conventionally available HPLC systems, such as the Agilent 1220, 1260 and 1290 Infinity LC Series or the Agilent 1100 HPLC series (all provided by the applicant Agilent Technologies—see www.agilent.com—which shall be incorporated herein by reference).

One embodiment of an HPLC system comprises a pumping apparatus having a piston for reciprocation in a pump working chamber to compress liquid in the pump working chamber to a high pressure at which compressibility of the liquid becomes noticeable.

One embodiment of an HPLC system comprises two pumping apparatuses coupled either in a serial or parallel manner. In the serial manner, as disclosed in EP 309596 A1, an outlet of the first pumping apparatus is coupled to an inlet of the second pumping apparatus, and an outlet of the second pumping apparatus provides an outlet of the pump. In the parallel manner, an inlet of the first pumping apparatus is coupled to an inlet of the second pumping apparatus, and an outlet of the first pumping apparatus is coupled to an outlet of the second pumping apparatus, thus providing an outlet of the pump. In either case, a liquid outlet of the first pumping apparatus is phase shifted, preferably essentially by 180 degrees, with respect to a liquid outlet of the second pumping apparatus, so that only one pumping apparatus is supplying into the system while the other is intaking liquid (e.g.

from the supply), thus allowing to provide a continuous flow at the output. However, it is clear that also both pumping apparatuses might be operated in parallel (i.e. concurrently), at least during certain transitional phases e.g. to provide a smooth(er) transition of the pumping cycles between the pumping apparatuses. The phase shifting might be varied in order to compensate pulsation in the flow of liquid as resulting from the compressibility of the liquid. It is also known to use three piston pumps having about 120 degrees phase shift. Also other types of pumps are known and operable in conjunction with the present invention.

The separating device preferably comprises a chromatographic column providing the stationary phase. The column might be a glass, metal, ceramic or a composite material tube (e.g. with a diameter from 50 µm to 5 mm and a length of 1 cm to 1 m) or a microfluidic column (as disclosed e.g. in EP 1577012 A1 or the Agilent 1200 Series HPLC-Chip/MS System provided by the applicant Agilent Technologies. The individual components are retained by the stationary phase differently and separate from each other while they are propagating at different speeds through the column with the eluent. At the end of the column they elute at least partly separated from each other. During the entire chromatography process the eluent might be also collected in a series of fractions. The stationary phase or adsorbent in column chromatography usually is a solid material. The most common stationary phase for column chromatography is silica gel, followed by alumina. Cellulose powder has often been used in the past. Also possible are ion exchange chromatography, reversed-phase chromatography (RP), affinity chromatography or expanded bed adsorption (EBA). The stationary phases are usually finely ground powders or gels and/or are microporous for an increased surface, which can be especially chemically modified, though in EBA a fluidized bed is used.

The mobile phase (or eluent) can be either a pure solvent or a mixture of different solvents. It can also contain additives, i.e. be a solution of the said additives in a solvent or a mixture of solvents. It can be chosen e.g. to adjust the retention of the compounds of interest and/or the amount of mobile phase to run the chromatography. The mobile phase can also been chosen so that the different compounds can be separated effectively. The mobile phase might comprise an organic solvent like e.g. methanol or acetonitrile, often diluted with water. For gradient operation water and organic is delivered in separate containers, from which the gradient pump delivers a programmed blend to the system. Other commonly used solvents may be isopropanol, THF, hexane, ethanol and/or any combination thereof or any combination of these with aforementioned solvents.

The sample fluid might comprise any type of process liquid, natural sample like juice, body fluids like plasma or it may be the result of a reaction like from a fermentation broth.

The fluid is preferably a liquid but may also be or comprise a gas and/or a supercritical fluid (as e.g. used in supercritical fluid chromatography—SFC—as disclosed e.g. in U.S. Pat. No. 4,982,597 A).

The pressure in the mobile phase might range from 2-200 MPa (20 to 2000 bar), in particular 10-150 MPa (100 to 1500 bar), and more particular 50-120 MPa (500 to 1200 bar).

The HPLC system might further comprise a detector for detecting separated compounds of the sample fluid, a fractionating unit for outputting separated compounds of the sample fluid, or any combination thereof. Further details of HPLC system are disclosed with respect to the aforementioned Agilent HPLC series, provided by the applicant Agilent Technologies, under www.agilent.com which shall be incorporated herein by reference.

Embodiments of the invention can be partly or entirely embodied or supported by one or more suitable software programs, which can be stored on or otherwise provided by any kind of data carrier, and which might be executed in or by any suitable data processing unit. Software programs or routines can be preferably applied in or by the control unit.

In the context of this application, the term "fluidic sample" may particularly denote any liquid and/or gaseous medium, optionally including also solid particles, which is to be analyzed. Such a fluidic sample may comprise a plurality of fractions of molecules or particles which shall be separated, for instance biomolecules such as proteins. Since separation of a fluidic sample into fractions involves a certain separation criterion (such as mass, volume, chemical properties, etc.) according to which a separation is carried out, each separated fraction may be further separated by another separation criterion (such as mass, volume, chemical properties, etc.), thereby splitting up or separating a separate fraction into a plurality of sub-fractions.

In the context of this application, the term "fraction" may particularly denote such a group of molecules or particles of a fluidic sample which have a certain property (such as mass, volume, chemical properties, etc.) in common according to which the separation has been carried out. However, molecules or particles relating to one fraction can still have some degree of heterogeneity, i.e. can be further separated in accordance with another separation criterion.

In the context of this application, the term "downstream" may particularly denote that a fluidic member located downstream compared to another fluidic member will only be brought in interaction with a fluidic sample or its components after interaction of those with the other fluidic member (hence being arranged upstream). Therefore, the terms "downstream" and "upstream" relate to a general flowing direction of the fluidic sample or its components, but do not necessarily imply a direct uninterrupted fluidic connection from the upstream to the downstream system parts.

In the context of this application, the term "sample separation apparatus" may particularly denote any apparatus which is capable of separating different fractions of a fluidic sample by applying a certain separation technique. Particularly, two separation units may be provided in such a sample separation apparatus when being configured for a two-dimensional separation. This means that the sample or any of its parts or subset(s) is first separated in accordance with a first separation criterion, and is subsequently separated in accordance with a second separation criterion, which may be the same or different.

The term "separation unit" may particularly denote a fluidic member through which a fluidic sample is guided and which is configured so that, upon conducting the fluidic sample through the separation unit, the fluidic sample or some of its components will be at least partially separated into different groups of molecules or particles (called fractions or sub-fractions, respectively) according to a certain selection criterion. An example for a separation unit is a liquid chromatography column which is capable of selectively retarding different fractions of the fluidic sample.

In the context of this application, the terms "fluid drive" or "mobile phase drive" may particularly denote any kind of pump or fluid flow source or supply which is configured for conducting a mobile phase and/or a fluidic sample along a fluidic path. A corresponding fluid supply system may be configured for metering two or more fluids in controlled proportions and for supplying a resultant mixture as a mobile phase. It is possible to provide a plurality of solvent supply lines, each fluidically connected with a respective reservoir containing a respective fluid, a proportioning appliance interposed between the solvent supply lines and the inlet of the fluid drive, the proportioning appliance configured for modulating solvent composition by sequentially coupling selected ones of the solvent supply lines with the inlet of the fluid drive, wherein the fluid drive is configured for taking in fluids from the selected solvent supply lines and for supplying a mixture of the fluids at its outlet. More particularly, one fluid drive can be configured to provide a mobile phase flow which drives or carries the fluidic sample through a respective separation unit, whereas another fluid drive can be configured to provide a further mobile phase flow which drives or carries the fluidic sample or its parts after treatment by respective separation unit, through a further separation unit.

BRIEF DESCRIPTION OF DRAWINGS

Other objects and many of the attendant advantages of embodiments of the present invention will be readily appreciated and become better understood by reference to the following more detailed description of embodiments in connection with the accompanied drawing(s). Features that are substantially or functionally equal or similar will be referred to by the same reference sign(s). The illustrations in the drawings are schematic.

FIGS. 7A-7D illustrate an embodiment with three sample reservoirs.

Referring now in greater detail to the drawings, FIG. 1 depicts a general schematic of a liquid separation system 10. A pump 20 receives a mobile phase from a solvent supply 25, typically via a degasser 27, which degases the mobile phase and thus reduces the amount of dissolved gases in it. The pump 20—as a mobile phase drive—drives the mobile phase through a separating device 30 (such as a chromatographic column) comprising a stationary phase. A sample dispatcher 40 (also referred to as sample introduction apparatus) is provided between the pump 20 and the separating device 30 in order to subject or add (often referred to as sample introduction) portions of one or more sample fluids into the flow of a mobile phase (denoted by reference numeral 200, see also FIG. 2). The stationary phase of the separating device 30 is adapted for separating compounds of the sample fluid, e.g. a liquid. A detector 50 is provided for detecting separated compounds of the sample fluid. A fractionating unit 60 can be provided for outputting separated compounds of sample fluid.

Figure 1:
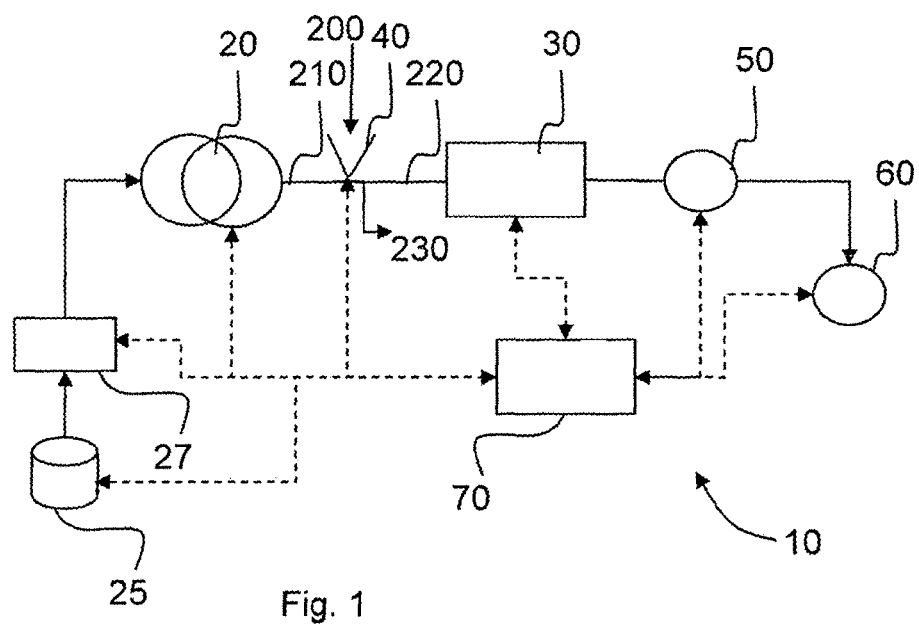
FIG. 1 shows a liquid separation system, in accordance with embodiments of the present invention, e.g. used in high performance liquid chromatography (HPLC).

While the mobile phase can be comprised of one solvent only, it may also be a mixture of a plurality of solvents. Such mixing might be a low pressure mixing and provided upstream of the pump 20, so that the pump 20 already receives and pumps the mixed solvents as the mobile phase. Alternatively, the pump 20 might be comprised of plural individual pumping units, with the pumping units each receiving and pumping a different solvent or mixture, so that the mixing of the mobile phase (as received by the separating device 30) occurs at high pressure and downstream of the pump 20 (or as part thereof). The composition (mixture) of the mobile phase may be kept constant over time, the so called isocratic mode, or varied over time, the so called gradient mode.

A data processing unit 70, which can be a conventional PC or workstation, might be coupled (as indicated by the dotted arrows) to one or more of the devices in the liquid separation system 10 in order to receive information and/or control operation. For example, the data processing unit 70 might control operation of the pump 20 (e.g. setting control parameters) and receive therefrom information regarding the actual working conditions (such as output pressure, flow rate, etc. at an outlet of the pump 20). The data processing unit 70 might also control operation of the solvent supply 25 (e.g. monitoring the level or amount of the solvent available) and/or the degasser 27 (e.g. setting control parameters such as vacuum level) and might receive therefrom information regarding the actual working conditions (such as solvent composition supplied over time, flow rate, vacuum level, etc.). The data processing unit 70 might further control operation of the sample dispatcher 40 (e.g. controlling sample introduction or synchronization of the sample introduction with operating conditions of the pump 20). The separating device 30 might also be controlled by the data processing unit 70 (e.g. selecting a specific flow path or column, setting operation temperature, etc.), and send —in return —information (e.g. operating conditions) to the data processing unit 70. Accordingly, the detector 50 might be controlled by the data processing unit 70 (e.g. with respect to spectral or wavelength settings, setting time constants, start/stop data acquisition), and send information (e.g. about the detected sample compounds) to the data processing unit 70. The data processing unit 70 might also control operation of the fractionating unit 60 (e.g. in conjunction with data received from the detector 50) and provide data back. Finally the data processing unit might also process the data received from the system or its part and evaluate it in order to represent it in adequate form prepared for further interpretation.

Figure 2:
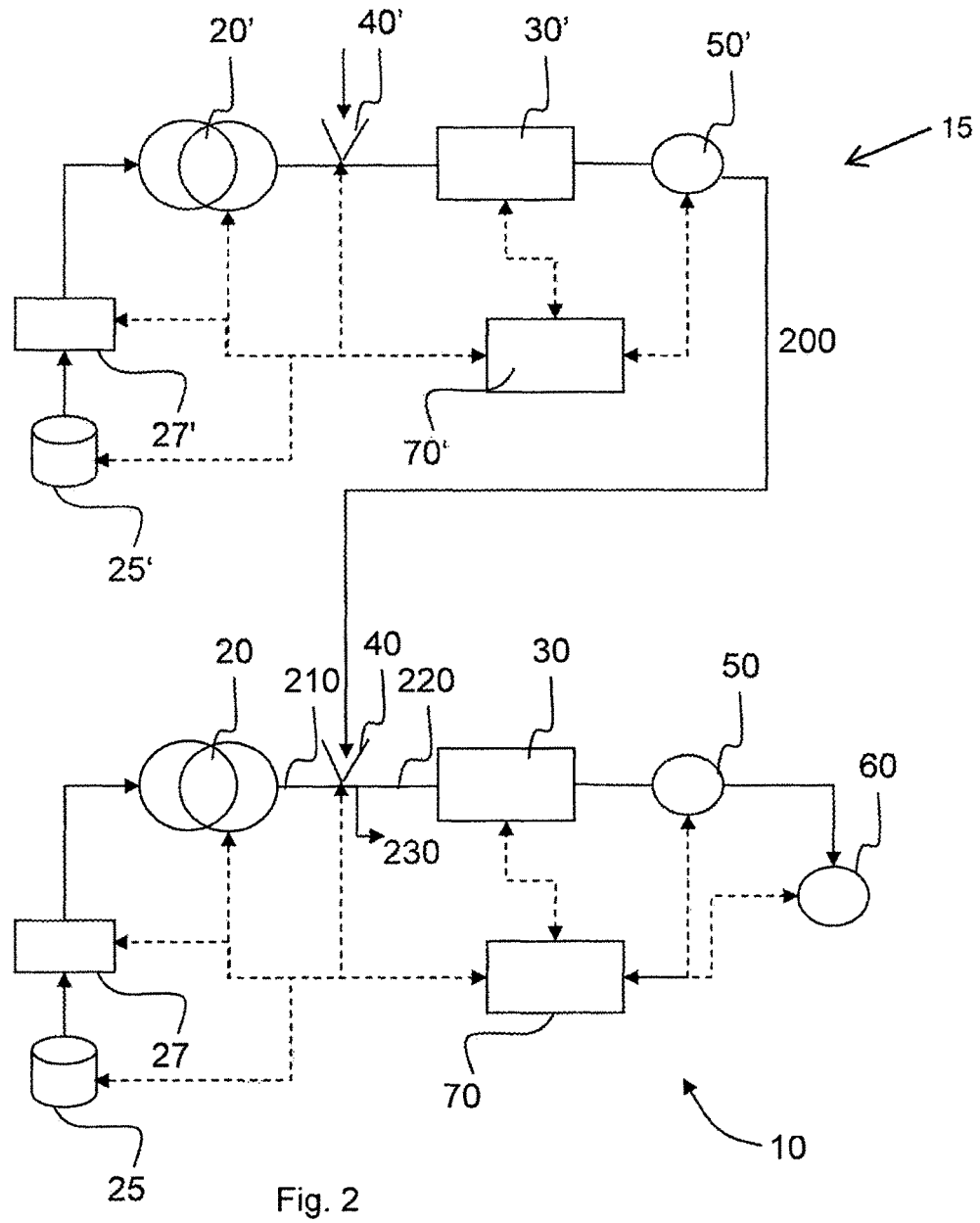
FIG. 2 shows an embodiment of the liquid separation system as used in 2D LC.

FIG. 2 schematically shows an embodiment of the liquid separation system 10 in accordance with the embodiment of FIG. 1 but further provided to be used in two-dimensional chromatography (2D LC). In 2D LC systems, usually the individual separations are operated independently. This means that there is one LC arrangement, which has a column for first dimension separation, of which the outlet fluid, e.g. a liquid (or parts or portions thereof) may be transferred into the high pressure path of the second dimension upstream of its column. If the separation in the second dimension is a periodic process, the fluid should only be introduced periodically and in portions (rather than continuously) into the high pressure path of the second dimension. This may lead to some complex arrangements. On one hand the arrangement should park or temporarily store a certain amount of fluid coming from the first dimension column and on the other hand it should bring the respective fluid plug or sniplet (which might be a fraction with regard to the sample of the first dimension and is a sample with regard to the second dimension) to the second dimension column with minimum disturbance.

As apparent from the schematic representation of FIG. 2, the liquid separation system 10 for 2D LC here consists of two parts, each of those substantially representing the liquid separation system as depicted in FIG. 1. The features of the first dimension 15 (also referred to as a separation subsystem) are denoted with ' and are identical in function with the corresponding features of the second dimension (denoted without '),except for the sampling unit 40'. The sampling unit 40' may represent a sample dispatcher similar in function to the sample dispatcher 40 or it may represent any other embodiment of a sampling unit such as an injection valve, manual injector, autosampler or the like. An output 200 from the second separating device 30' (either provided directly or with an optional detector 50' coupling thereto) is output (at low pressure) and coupled to the sample dispatcher 40. The output 200, or at least a part thereof, of the first dimension thus provides the input of the sample dispatcher 40 and can be introduced or transferred (modulated) into the second dimension.

It is clear that the first dimension may be provided in a simpler form and with fewer components than shown in FIG. 2. For example the detector 50' can be omitted, and the data processing unit 70' might be the same as 70.

In both FIGS. 1 and 2, the flow path from the pump 20 to the sample dispatcher 40 shall be denoted as 210, the flow path from the sample dispatcher 40 to separating device shall be denoted as 220, and an additional flow path to waste shall be denoted as 230.

FIGS. 3A to 3D schematically show different sequential states of operation of the sample dispatcher 40. A full operation cycle may comprise a sequence of states 3A to 3D, and subsequently 3D to 3A in the reversed sequence. Each of the states 3B to 3C can differ in function depending on the sequentially previous state, as will be explained further in detail.

The sample dispatcher 40 comprises a valve 300 (which might be embodied by any suitable valve or combination of valves, as known in the art), a first sample reservoir 310, and a second sample reservoir 320. Each of the first and second sample reservoirs 310 and 320 is configured for receiving and temporarily storing a respective sample fluid portion from the sample fluid line referenced by numeral 200.

The valve 300 in FIG. 3 is schematically represented here as a shift valve for the sake of better understanding. Other embodiments in rotational valves are described later with respect to FIGS. 4-7.

Figure 3A:
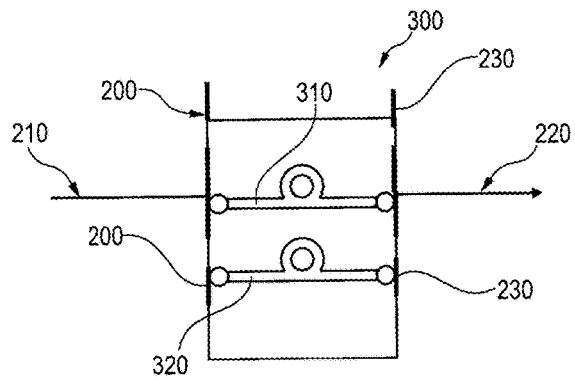
FIGS. 3A to 3D schematically show different states of operation of a sample dispatcher.

The different states of operation of the valve 300 and thus the different modes or phases of operation of the sample dispatcher 40 shall be explained in the following. FIG. 3A shall represent a (starting) state wherein the first sample reservoir 310 is coupled between lines 210 and 220, i.e. between the pump 20 and the column 30, so that the content of the first sample reservoir 310 can be provided (also referred to as injected or introduced) into the flow path (and thus into the flow of the mobile phase) and will be moved downstream to the column 30 for separation. The mobile phase from the line 210 is provided via the reservoir 310 and the line 220 to a separation unit 30 to facilitate the separation. The second sample reservoir 320 is coupled to line 200 and may thus be filled (or loaded) with a new sample fluid portion. The other side of the second sample reservoir 320 is connected to waste 230.

Figure 3B:
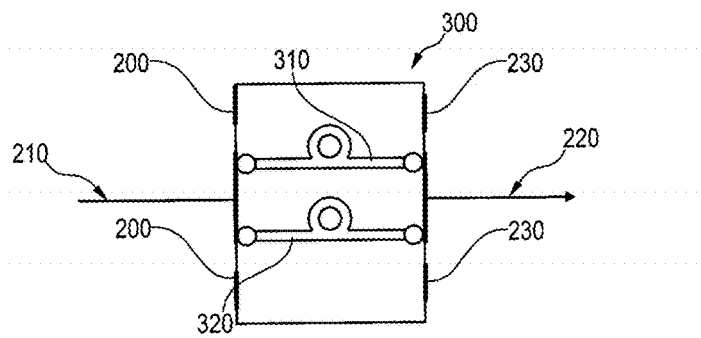

FIG. 3B shows a "dilution state" in respect to the sample reservoir 320. In this dilution state, the first sample reservoir 310 and the second sample reservoir 320 are coupled between lines 210 and 220, i.e. coupled in parallel between the pump 20 and the column 30, so that a portion of the mobile phase provided from the pump 20 passes through the second sample reservoir 320 and another portion passes through the first sample reservoir 310. Accordingly, the content of the second sample reservoir 320 (which is sample portion which has been filled in e.g. during the state of FIG. 3A) will gradually be displaced into the line 220 and diluted by the mobile phase flown through the first sample reservoir 310 as both partial flows (via the second reservoir 320 and via the first sample reservoir 310) are joined, so that the content of the second sample reservoir 320 gets diluted (e.g. with respect to the state in FIG. 3A). This is in particular useful in 2D LC applications, e.g. of FIG. 2, thus allowing to adapt and modify concentration of solvents to the respective application. The dilution state may be maintained at least for a time interval sufficient for displacement of at least part of the content of the first and second sample reservoirs 310, 320 simultaneously into the common fluid conduit 220. Composition of the sample fluid portion that has been temporarily stored in the second sample reservoir 320 (e.g. as showing in FIG. 3A) is changed by mixing with the content displaced out of the first sample reservoir 310 as both fluids enter the common fluid line 220.

Figure 3C:
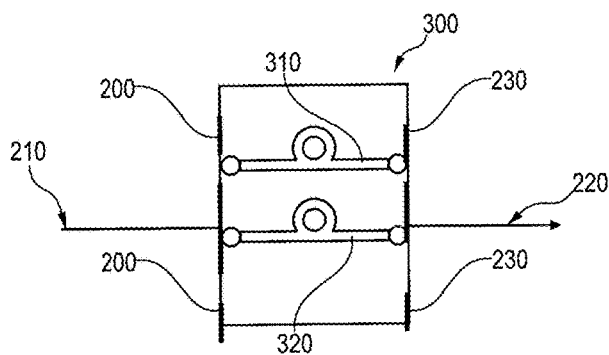
Figure 3D:
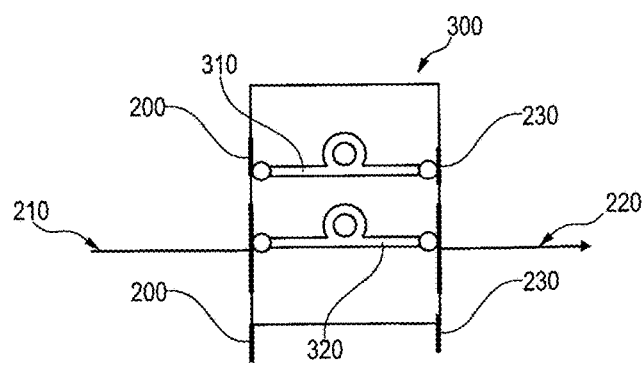

FIG. 3C shows an "intermediate discharge state" e.g. following after the state shown in the FIG. 3B. In such intermediate state, only the second sample reservoir 320 is coupled between lines 210 and 220, i.e. coupled between the pump 20 and the column 30, while the first sample reservoir 310 is decoupled or not yet coupled e.g. between lines 210 and 230 (as shown in FIG. 3D). However, though the sample reservoir 310 is yet not (completely) coupled between the lines 210 and 230, the connection to the line 230 is already at least partly established. By that any compressed content of the sample reservoir 310, as it comes e.g. from the state of FIG. 3B, can be decompressed into the line 230 (and thus e.g. to waste), thus releasing the high pressure within the reservoir 310 and preventing possible adverse effects or even damage to the system components connected flow upstream of the line 210.

FIG. 3D shows a state which substantially symmetrically corresponds to the state of FIG. 3A with the difference that in FIG. 3D the second sample reservoir 320 is now coupled between the lines 210 and 220 and thus between the pump 20 and the column 30, while the first sample reservoir 310 is coupled to line 200 and may thus be filled with the portion of sample via line 200.

Controlling the time period of dilution state like in the FIG. 3B allows control over dilution of the content of the second sample reservoir 320 with the mobile phase as it is transferred into the line 220 and further downstream the flow path towards the separation unit 30. It goes without saying that such dilution will only occur unless the sample fluid content stored in the second sample reservoir 320 has been completely displaced out of the reservoir 320 (or at least as long as sample fluid content stored in the second sample reservoir 320 will be being moved therefrom).

The sequence of states 3A to 3D may represent a part of a switching or dispatching cycle corresponding to switching from the state of filling the second sample reservoir 320 and transferring the content of the first sample reservoir 310 into the line 220 towards the state of filling the first sample reservoir 310 and transferring the content of the second sample reservoir 320 into the line 220. The other (also referred to as "second") part of the switching cycle comprising switching from the state 3D towards the state 3A is principally symmetrical to the aforedescribed part of the switching cycle in respect to the role of the reservoirs 310, 320. A graphical representation of a state comprised in the second part of the cycle and functionally symmetrical to the state of FIG. 3C of the aforedescribed part of the cycle has been omitted in the FIG. 3. The state of FIG. 3C when occurring during the second part of the cycle is not linked to any special function.

It is clear that the valve 300 may be operated to sequentially move between the states 3A to 3D and then return by moving between the states 3D to 3A, and so on. However, any other sequence of operation may be applied accordingly dependent on the specific application.

In the embodiment of FIG. 3, the dilution state of FIG. 3B may preferably be applied only for a short term, because in such state the flow 200 (e.g. from the first dimension) is blocked.

In all states of FIGS. 3, at least one of the sample reservoirs 310, 320 is coupled between lines 210 and 220, i.e. between the pump 20 and the column 30, so that pressure variations (e.g. pressure drops) occurring at line 220 to the column 30 can be avoided (or at least reduced) e.g. when switching between different states. In other words, essentially at any point in the time during operation at least one of the sample reservoirs 310 and 320, either alone or in a parallel combination, is coupled between the mobile phase drive 20 and the separation unit 30.

FIGS. 4A-4F show an embodiment of the valve 300 as a rotational valve. Rotational valves are readily known in the art and need not to be explained in detail here. The rotational valve 300 of FIG. 4 comprises a stator element with a plurality of terminals or ports (indicated as circles) 400A-400H, and a rotor element comprising a plurality of flow couplers, which are embodied here as grooves 410A-410D. The grooves 410A-410D here are circular segment grooves which are circular segments (here arranged in two different diameters) of the valve 300. Grooves 410A and 410B are arranged along an inner circle of the valve 300 for respectively coupling the terminals situated in this inner circle, namely terminals 400A-400D. Grooves 410C and 410D are arranged along an outer circle of the valve 300 for respectively coupling the terminals situated in this outer circle, namely terminals 400E-400H.

Figure 4A:
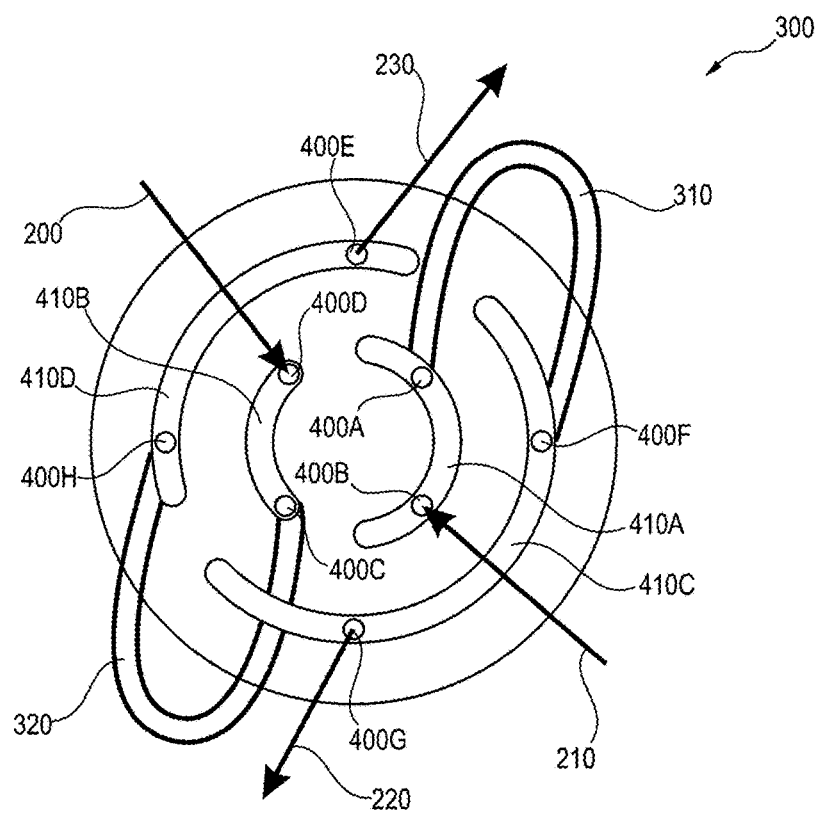
FIGS. 4A-4F show an embodiment of a valve as a rotational valve.

In the representations of FIGS. 4A-4F, the stator element is shown in the same position, while the rotor element is rotated clockwise in the direction from FIG. 4A towards 4F. The same kind of representation will also be applied in FIGS. 5-6 respectively, with the stator element being shown in the same position, while the rotor element is rotated clockwise in the direction from respective FIGS. 5A to 5C and FIGS. 6A to 6C. In FIGS. 7 the schematic rotor is rotated counter-clockwise.

In the embodiment of the switching valve 300 of FIG. 4, the ports 400A-400H are arranged symmetrically. In the outer circle, the groove 410C is longer than the groove 410D, and accordingly the groove 410A in the inner circle is longer than groove 410B. The elongated grooves allow coupling both sample reservoirs 310 and 320 in parallel.

Figure 4B:
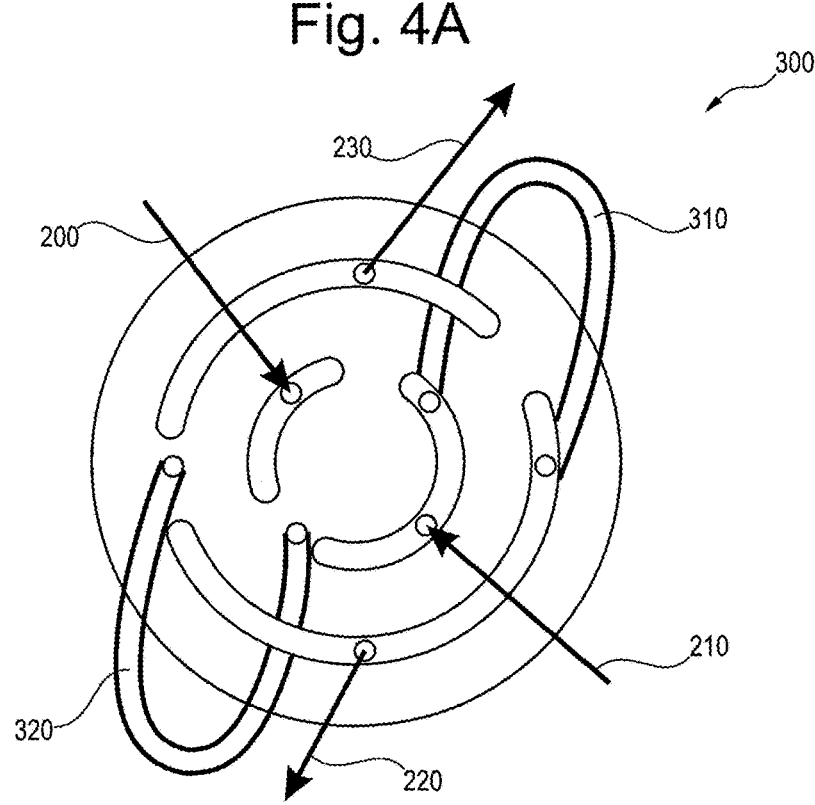
Figure 4C:
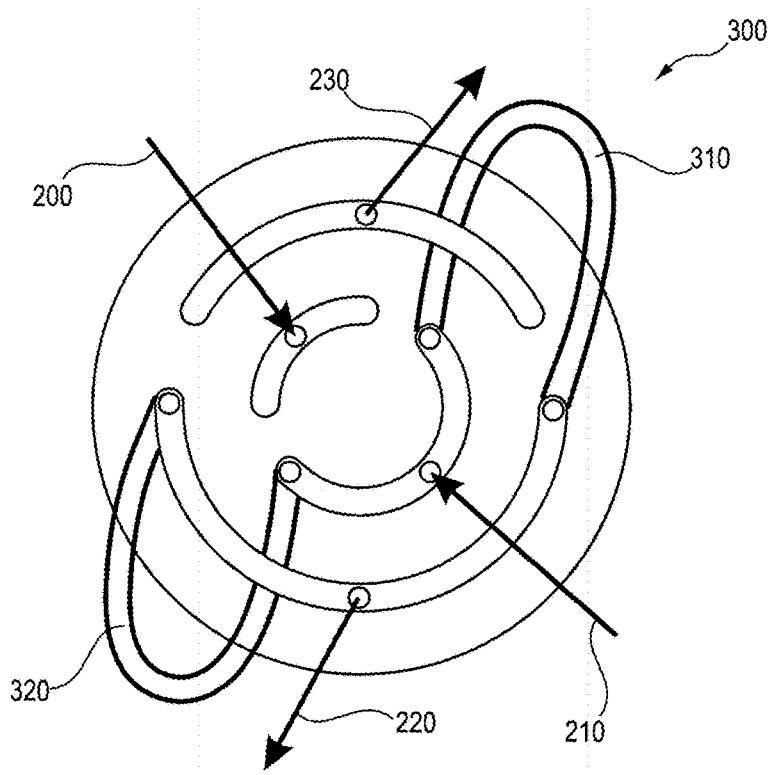
Figure 4D:
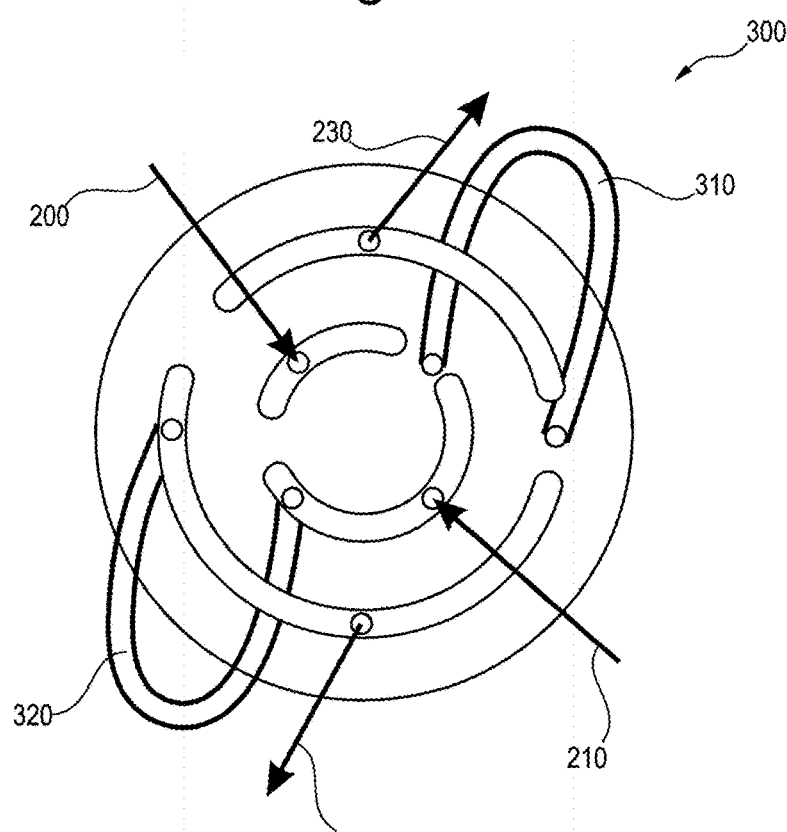
Figure 4E:
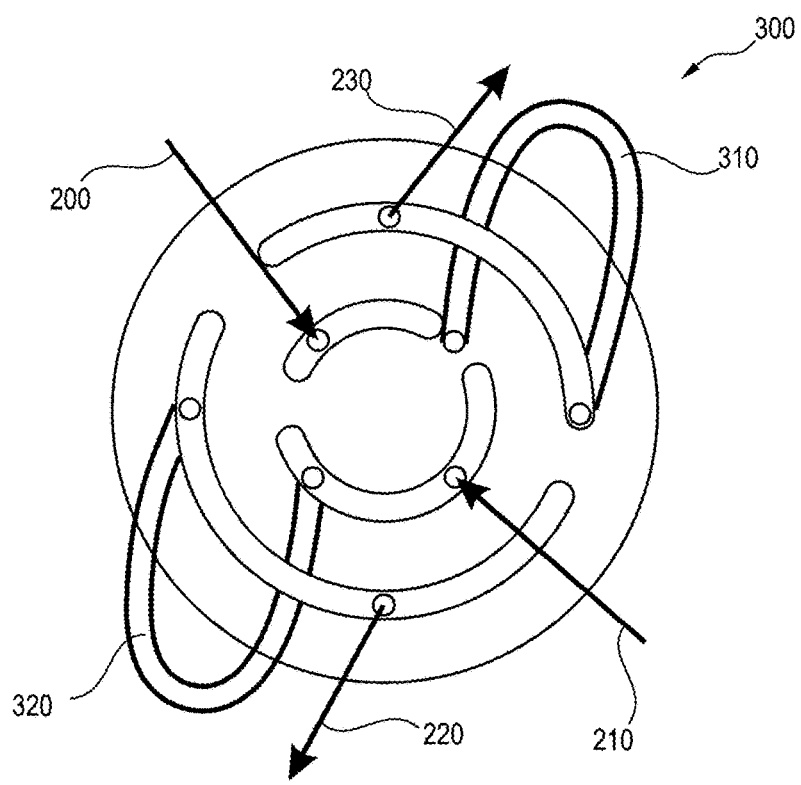
Figure 4F:
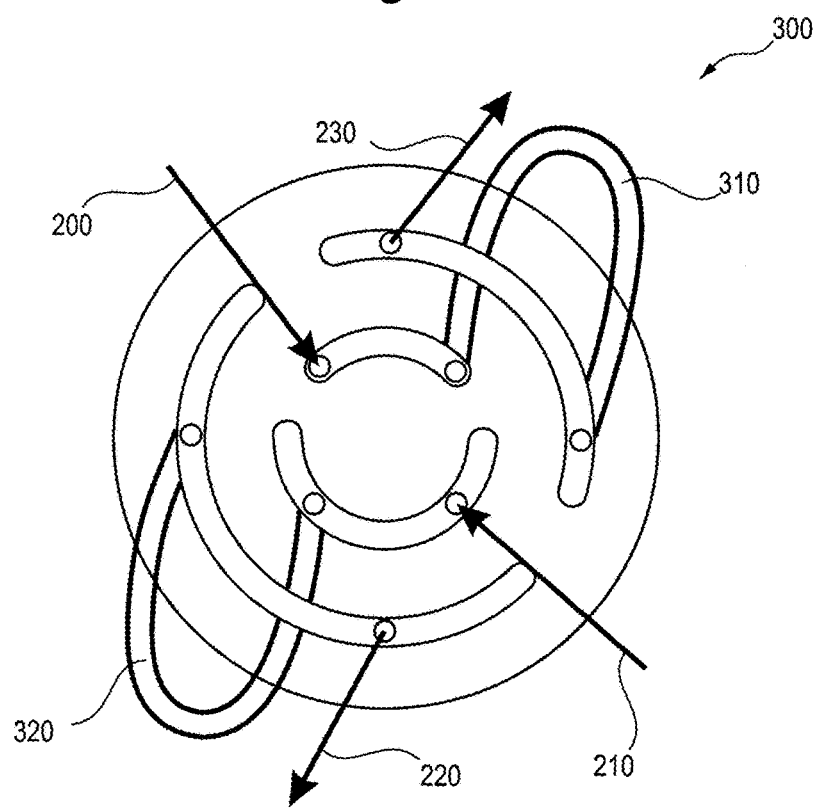

The states of operation in FIG. 3 and FIG. 4 substantially match, so that FIGS. 3A and 4A show the same functional state, FIGS. 3B and 4C show the same functional state, FIGS. 3C and FIG. 4E show the same functional state, and FIGS. 3D and 4F show the same functional state. The aforesaid with respect to FIG. 3 applies accordingly, mutatis mutandis, to the corresponding figures in FIG. 4 and need not be repeated. Additionally, the respective fluid flows are also indicated by arrows in FIG. 4.

FIGS. 4B and 4D depict transitional states passed by the rotor during rotation. During these states, either of the sample reservoirs 310, 320 is temporarily decoupled from any fluidic connections on both ends. The corresponding transitional states are not explicitly shown in the FIG. 3 and are only shown for better illustration of the rotational movement of the rotor in the FIG. 4.

Figure 5A:
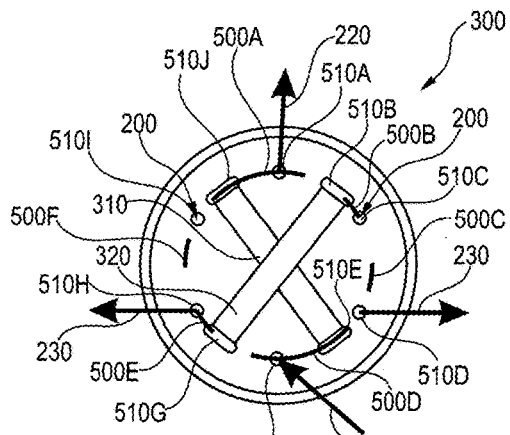
FIGS. 5A-5C illustrate another embodiment of a rotational valve.
Figure 5B:
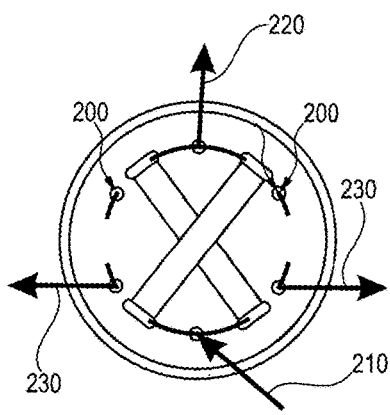
Figure 5C:
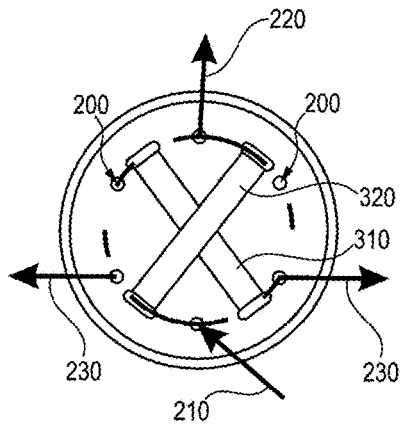

FIGS. 5A-5C illustrate another embodiment of a rotational valve 300. This embodiment has 10 ports 510A-510J (indicated by circles; and those connecting to the sample reservoirs—by elongated circles) and 6 grooves 500A-500F (situated in one radius only).

The FIGS. 5 represent sequential rotational states of one of the possible embodiments of such modulation valve, which correspond to those described in the FIGS. 3 in function, namely FIG. 5A corresponds in function to FIG. 3A, FIG. 5B to FIG. 3B, and FIG. 5C to FIG. 3D. The functionally symmetrical part of the switching cycle corresponding to the state sequence of FIGS. 5C, 5B, 5A corresponds to that already explained above on example of FIGS. 3. States corresponding to e.g. FIG. 3C are not explicitly shown in the FIGS. 5.

Figure 6A:
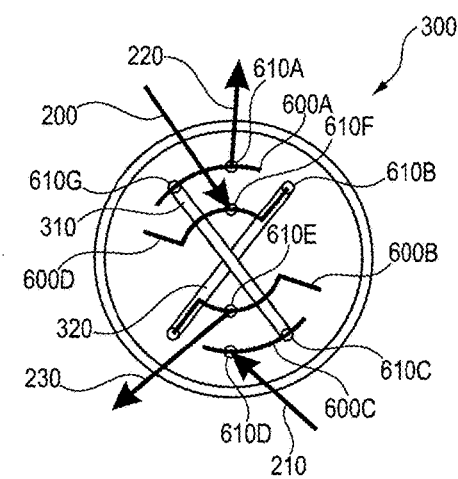
FIGS. 6A-6C illustrate a further embodiment of a rotational valve.
Figure 6B:
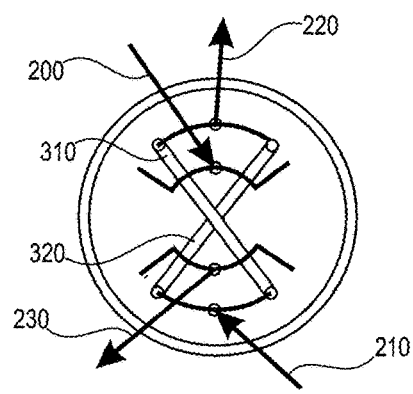
Figure 6C:
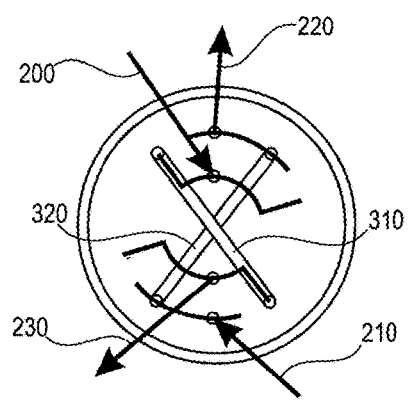

FIGS. 6A-6C illustrate a further embodiment of a rotational valve 300. This embodiment has 8 ports 610A-61OG (indicated by circles) and 4 grooves 600A-600D. FIGS. 6 also represent sequential rotational states of one of the possible embodiments of such modulation valve, which correspond to those described in the FIG. 3 in function, namely FIG. 6A corresponds in function to FIG. 3A, FIG. 6B to FIG. 3B, and FIG. 6C to FIG. 3D. The functionally symmetrical part of the switching cycle corresponds to that already explained above on example of FIGS. 3.

It is clear that the line 200 providing the sample might generally originate from diverse sources, such as a previous dimension separation (e.g. LC, CE, centrifugation), process liquid supply, sewage control line etc.

Reservoirs 310, 320 may have additional superimposed functions, e.g. be implemented as trapping columns, SPE cartridges, chemical reactors, etc.

The corresponding sample dispatcher 40 embodiments might comprise not only two (as shown in FIGS. 3-6) but three or even more sample reservoirs operated in a manner as described above or similar, with at least one sample reservoir being operated for sample transfer and at least one sample reservoir being filled in any of the non-transition states. The above examples of FIGS. 3-6 have been shown for the sake of better understanding with two sample reservoirs 310, 320 only. However, it is clear that the same principles apply, mutatis mutandis, in case of three or more sample reservoirs.

FIGS. 7A-7D schematically illustrate an embodiment of the sample dispatcher 40 with three sample reservoirs 310, 320, and 700 (also denoted with numerals 1-3 for the sake of better understanding). The states from FIG. 7A to FIG. 7D are the following.

FIG. 7A represents a working state for the second sample reservoir 320. The first sample reservoir 310 is receiving sample, the second sample reservoir 320 is in analysis (i.e. between pump 20 and separation unit 30), and the third sample reservoir 700 is resting.

FIG. 7B represents a transition state. The first sample reservoir 310 is in transfer to analysis, the second sample reservoir 320 is still in analysis, and the third sample reservoir 700 is discharging pressure.

FIG. 7C represents a dilution state for the first sample reservoir 310. The first sample reservoir 310 and the second sample reservoir 320 are in parallel between pump 20 and separation unit 30, and the third sample reservoir 700 is receiving sample.

FIG. 7D represents a working state for the first sample reservoir 310. The third sample reservoir 700 is receiving sample, the first sample reservoir 310 is in analysis (i.e.

between pump 20 and separation unit 30), and the second sample reservoir 320 is resting.

Further rotation of the schematic valve part with the sample reservoirs 310, 320, 700 will in turn sequentially pass through the sequence of the states analogous to that described for the three reservoirs 310, 320, 700 one after the other.

The embodiment with three or even more reservoirs 310, 320, 700 allows to have at least two reservoirs connected in parallel in the dilution state, while the respectively third reservoir is being filled with the sample fluid. Thus the duration of the dilution state may no longer be limited by the fact that the sample providing line 200 is blocked as e.g. in the case of the embodiments of FIGS. 3-6 with two reservoirs 310, 320.

It is clear that the connection scheme of the valve 300 in the embodiments shown in FIGS. 3-7 may also be applied differently. For example, exchanging lines 210 and 220 allows using the sample dispatcher 40 in so-called co-current or counter-current mode as known in the art. For example, in order to minimize dispersion in the sample zone when passing through a respective sample reservoir, it is preferable to operate in counter-current mode, which means that the sample is moved out of a respective sample reservoir via the same reservoir terminal as it was filled. FIGS. 5 and 6 illustrate the counter-current mode. To realize the counter-current mode in FIGS. 3, 4 and 7, the lines 210 and 220 providing and receiving the mobile phase flow should be exchanged.

The co-current mode is represented in the FIGS. 3, 4 and 7. This mode is advantageous if additional dilution caused by dispersion of the sample portion is desired. In this case the flow direction of the sample fluid flow as it is filled and of the mobile phase flow as it transports the sample fluid out of the reservoir are configured to be the same in respect to a respective sample reservoir. Thus the sample is forced to pass through the entire length of the sample reservoir and to leave it from the respectively other end than the end where the sample was filled from, which may cause e.g. additional sample dispersion and dilution within the sample reservoir.

The invention claimed is:

1. A sample dispatcher configured for individually introducing a plurality of portions of one or more sample fluids into a flow of a mobile phase of a separation system configured for separating compounds of the sample fluids, wherein the separation system comprises a mobile phase drive configured for driving the mobile phase through a separation unit configured for separating compounds of the sample fluids in the mobile phase, the sample dispatcher comprising:
a plurality of sample reservoirs, each configured for receiving and temporarily storing a respective sample fluid portion or at least a part thereof;
wherein the sample dispatcher is configured for selectively coupling one of the plurality of sample reservoirs between the mobile phase drive and the separation unit; and
the sample dispatcher is further configured for coupling at least two of the plurality of sample reservoirs in parallel between the mobile phase drive and the separation unit.

2. The sample dispatcher of claim 1, wherein:
the sample dispatcher is configured for coupling at least two of the plurality of sample reservoirs in parallel between the mobile phase drive and the separation unit during a dilution state of changing from having one of the plurality of sample reservoirs being coupled between the mobile phase drive and the separation unit to further having another one of the plurality of sample reservoirs being coupled between the mobile phase drive and the separation unit.

3. The sample dispatcher of claim 2, wherein the sample dispatcher is configured for at least one of:
diluting the respective sample fluid portion with the mobile phase during the dilution state;
maintaining the dilution state at least for a time interval sufficient for displacement of at least a part of the content of the plurality of sample reservoirs, coupled between the mobile phase drive and the separation unit, simultaneously into a common fluid conduit;
changing composition of a respective sample fluid portion that has been stored in one of the plurality of sample reservoirs by mixing with the content displaced out of another of the plurality of sample reservoirs into a common conduit;
pressure relief of a respective sample reservoir after having been coupled between and subsequently decoupled from the mobile phase drive and the separation unit and before being coupled for receiving and temporarily storing a respective sample fluid portion or at least a part thereof;
precompressing a respective sample reservoir before being coupled between the mobile phase drive and the separation unit and after being coupled for receiving and temporarily storing a respective sample fluid portion or at least a part thereof.

4. The sample dispatcher of claim 1, wherein:
the sample dispatcher is configured so that essentially at any point in the time at least one of the plurality of sample reservoirs, either alone or in a parallel combination, is coupled between the mobile phase drive and the separation unit.

5. The sample dispatcher of claim 1, wherein:
the sample dispatcher receives the plurality of portions of one or more sample fluids and is configured for loading a respective sample fluid portion into at least one of the plurality of sample reservoirs.

6. The sample dispatcher of claim 1, comprising:
a switching valve having a plurality of ports and a plurality of flow couplers, wherein:
each port is configured for coupling a fluid flow path to the switching valve;
each flow coupler is configured for fluidically coupling between at least two of the ports;
the switching valve can be selectively operated between a plurality of different states;
in each different state at least one of the flow couplers is fluidically coupling to a different port;
the mobile phase drive is coupled to a first port of the plurality of ports, the separation unit is coupled to a second port of the plurality of ports, a flow path for receiving the plurality of portions of the one or more sample fluids is coupled to a third port of the plurality of ports, the first sample reservoir is coupled to a forth and to a fifth port of the plurality of ports, and the second sample reservoir is coupled to a sixth and to a seventh port of the plurality of ports; and
a first one of the flow couplers is configured for coupling between the second, fifth and the sixth ports, and a second one of the flow couplers is configured for coupling between the first, fourth and seventh ports, so that at least two of the plurality of sample reservoirs are coupled in parallel between the mobile phase drive and the separation unit.

7. The sample dispatcher of claim 6, wherein:
a first subset of the plurality of ports is arranged along an inner circle;
a second subset of the plurality of ports is arranged along an outer circle having larger diameter than the inner circle;
a first subset of the plurality of flow couplers is configured to couple between ports of the first subset of the plurality of ports; and
a second subset of the plurality of flow couplers is configured to couple between ports of the second subset of the plurality of ports.

8. The sample dispatcher of claim 7, wherein:
the first subset of the plurality of ports has four ports;
the second subset of the plurality of ports has four ports;
the first subset of the plurality of flow couplers has two flow couplers; and
the second subset of the plurality of flow couplers has two flow couplers.

9. The sample dispatcher of claim 8, wherein:
the plurality of ports are arranged symmetrically; and
one of the flow couplers in each of the first and second subsets of the plurality of flow couplers is longer than the other in the same subset.

10. A separation system for separating sample fluid compounds, the separation system comprising:
a first mobile phase drive configured to drive a first mobile phase through the separation system;
a sample providing apparatus being configured to provide a plurality of portions of one or more sample fluids;
a sample dispatcher of claim 1 being coupled to the first mobile phase drive and to the sample providing apparatus, and being configured to introduce the provided sample fluid portions into a flow of the first mobile phase; and
a first separation unit configured for separating compounds of the sample fluid in the first mobile phase,
wherein the sample dispatcher is configured to load a respective sample fluid portion into at least one of the one or more sample reservoirs.

11. The separation system of claim 10, further comprising at least one of:
a detector configured to detect separated compounds of the sample fluid;
a collection unit configured to collect separated compounds of the sample fluid;
a data processing unit configured to process data received from the separation system;
a degassing apparatus for degassing the mobile phase.

12. The separation system of claim 10, wherein the sample providing apparatus comprises:
a second mobile phase drive configured to drive a second mobile phase through a separation subsystem; and
a second separation unit configured for separating compounds of the sample fluid in the second mobile phase,
wherein at least a portion of the separated compounds are provided to the sample dispatcher as the plurality of portions of one or more sample fluids.

13. A method of individually introducing a plurality of portions of one or more sample fluids into a flow of a mobile phase of a separation system configured for separating compounds of the sample fluids, wherein the separation system comprises: a mobile phase drive configured for driving the mobile phase through a separation unit configured for separating compounds of the sample fluids in the mobile phase, and a sample dispatcher having a plurality of sample reservoirs, each configured for receiving and temporarily storing a respective sample fluid portion or at least a part thereof, the method comprising:
selectively coupling one of the plurality of sample reservoirs between the mobile phase drive and the separation unit; and
coupling at least two of the plurality of sample reservoirs in parallel between the mobile phase drive and the separation unit.

14. The method of claim 13, further comprising:
coupling at least two of the plurality of sample reservoirs in parallel between the mobile phase drive and the separation unit during a dilution state of changing from having one of the plurality of sample reservoirs being coupled between the mobile phase drive and the separation unit to further having another one of the plurality of sample reservoirs being coupled between the mobile phase drive and the separation unit.

15. The method of claim 14, further comprising at least one of:
diluting the respective sample fluid portion with the mobile phase during the dilution state;
maintaining the dilution state at least for a time interval sufficient for displacement of at least a part of the content of the plurality of sample reservoirs, coupled between the mobile phase drive and the separation unit, simultaneously into a common fluid conduit;
changing composition of a respective sample fluid portion received in one of the plurality of sample reservoirs by mixing with the content displaced out of the other of the plurality of sample reservoirs;
pressure relief of a respective sample reservoir after being coupled between and subsequently decoupled from the mobile phase drive and the separation unit and before being coupled for receiving and temporarily storing a respective sample fluid portion or at least a part thereof;
precompressing a respective sample reservoir before being coupled between the mobile phase drive and the separation unit and after being coupled for receiving and temporarily storing a respective sample fluid portion or at least a part thereof.

16. The method of claim 13, further comprising:
coupling at least one of the plurality of sample reservoirs, either alone or in a parallel combination, between the mobile phase drive and the separation unit.

17. A non-transitory computer readable storage medium comprising instructions stored thereon, that when executed by a computer, control or perform the method of claim 13.

* * * * *